United States Patent
Murata et al.

[19]

[11] Patent Number: 6,166,784
[45] Date of Patent: *Dec. 26, 2000

[54] IMAGING OPTICAL SYSTEM

[75] Inventors: Akiko Murata; Katsuya Ono, both of Hachioji, Japan

[73] Assignee: Olympus Optical Company, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/871,763

[22] Filed: Jun. 9, 1997

[30] Foreign Application Priority Data

Jun. 7, 1996 [JP] Japan .................................. 8-145522
Jun. 3, 1997 [JP] Japan .................................. 9-145036

[51] Int. Cl.[7] .............................. G02F 1/13; G02F 1/133
[52] U.S. Cl. ...................................... 349/1; 349/1; 349/33
[58] Field of Search ................ 349/1, 33; 359/FOR 105, 359/114, FOR 126, FOR 134, FOR 131

[56] References Cited

U.S. PATENT DOCUMENTS 4,190,330  2/1980  Berreman ............................... 350/331
4,679,911  7/1987  Jacobs et al. ......................... 350/347 E
5,071,229  12/1991  Oaki et al. ................................ 359/53

FOREIGN PATENT DOCUMENTS 6-235090  10/1980  Japan .
2-46423   2/1990   Japan .

*Primary Examiner*—Frank G. Font
*Assistant Examiner*—Michael P. Stafira
*Attorney, Agent, or Firm*—Stevens, Davis, Miller & Mosher, L.L.P.

[57] ABSTRACT

An imaging optical system is disclosed. The system comprises a liquid crystal lens including a first body consisting of a substantially transparent birefringent liquid crystal member, a second body consisting of a substantially transparent birefringent liquid crystal member, and two pairs of electrodes for adding an electric field or a magnetic field onto the first body and the second body. A rear face of the first body is aligned perpendicular to a front face of the second body, the first body and the second body have substantially symmetrical shape against a plane perpendicular to an optical axis and plurality of optical elements are arranged front and after the liquid crystal lens.

19 Claims, 10 Drawing Sheets

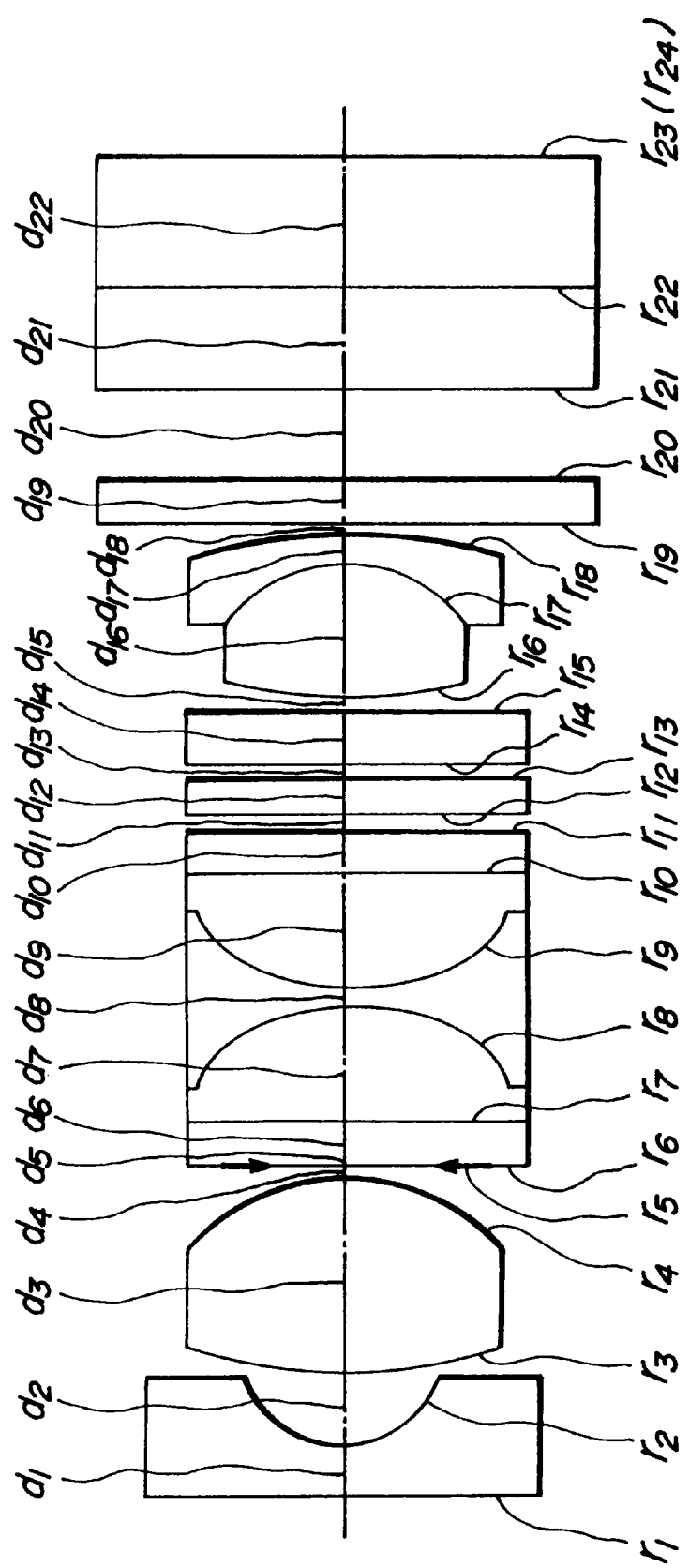

FIG_10
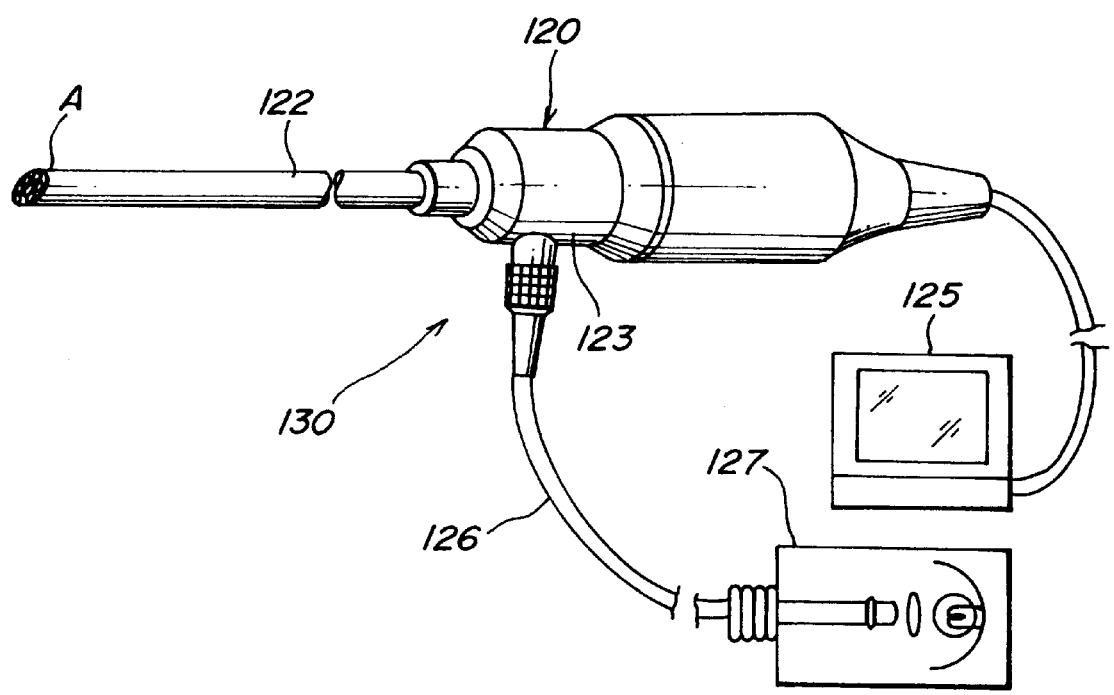

IMAGING OPTICAL SYSTEM

BACKGROUND OF THE INVENTION

1. Field of the Invention

The present invention relates to an imaging optical system having variable focusing function for an imaging lens, more particularly to an imaging optical system for use in an endoscope which is functioning as a variable focusing element and is useful in case of constructing an imaging element required for a compact imaging optical system, such as an endoscope or the like.

2. Related Art Statement

As a conventional imaging optical system for use in an endoscope for an imaging lens or the like having automatic infocusing switching function, there is an imaging optical system described in, for example, Japanese Patent Application Publication No. 35,090/87. This publication discloses that a holding frame of an objective lens mounted within a range of a distal hard portion of the endoscope is so formed as to extend the frame in the longitudinal direction, thereby moving the frame back and forth mechanically in the longitudinal direction by the operation for focusing adjusting at proximal operating section, resulting in a change of a pint position.

In the conventional imaging optical system disclosed in Japanese Patent Application Opened No. 46,423/90, the imaging optical system comprises a mechanism for selecting poplarizing directions and a variable focusing lens utilizing an electro-optical effect of a liquid crystal, thereby changing the focal length of the objective lens by an electrical drive.

The above conventional imaging optical system disclosed in Japanese Patent Application Publication No. 35,090/87, disclosed that the mechanism for moving the holding frame mechanically is accommodated in a minimum space, such as a distal hard section for the endoscope, but it is substantially impossible to obtain such a construction due to the spatial restriction.

The above conventional imaging optical system disclosed in Japanese Patent Application Publication No. 46,423/90, has a requirement of a function for selecting the polarizing directions in order to prevent double images from being generated due to the birefringent of the liquid crystal, so that transmittance of the vari-focus lens becomes decreased to 50% or less. Such a decrease of light quantity becomes fatal to the lens for an endoscope, so that usually, as a countermeasure, the diameter of an aperture diaphragm is increased or the diameter of light guide is increased. The former, however, has a defect that the focal depth becomes shallow, and the later has a defect in that as the diameter of the endoscope itself increases. Therefore, both countermeasures are not practical to accommodate such variable focusing function in the endoscope.

SUMMARY OF THE INVENTION

It is an object of the present invention to eliminate the above described disadvantages of the conventional imaging optical system.

It is another object of the present invention to provide a minimized and space saved imaging optical system for use in such as an endoscope, which has a variable focusing function with about a 100% transmitting factor in the far point infocusing condition and in the near point infocusing condition without an accompanying decrease of light quantity, thereby improving the depth of focus and brightness, and thus, obtaining the possibility of magnified observation.

According to a first aspect of the present invention, there is provided an imaging optical system comprising an optical member including a first body consisting of a substantially transparent birefringent liquid crystal member, a second body consisting of a substantially transparent birefringent liquid crystal member, and at least a pair of electrodes for adding an electric field or a magnetic field onto the first body and the second body, a rear face of the first body being aligned perpendicular to a front face of the second body, and the first body and the second body having substantially symmetrical shape against a plane perpendicular to an optical axis.

According to the present invention, the imaging optical system comprises an optical member including a first body consisting of a substantially transparent birefringent liquid crystal member, a second body consisting of a substantially transparent birefringent liquid crystal member, and at least a pair of electrodes for adding an electric field or a magnetic field onto whole the first body and the second body, a rear face of the first body being aligned perpendicular to a front face of the second body, so that if such an imaging optical system is loaded as an imaging optical system for an endoscope, a variable focusing function can be added to the endoscope without any requiring a polarizing plate.

That is, according to the present invention, in the condition that a voltage is not applied to the member, an incident light having a polarizing direction perpendicular to a major axis direction of the liquid crystal at an incident end of the first liquid crystal body is subjected to an effect due to ordinary ray refractive index of the liquid crystal in the first body, and is subjected to an effect due to extra-ordinary ray refractive index in the second liquid crystal body, in which the major axis direction of the liquid crystal at the incident end is orthogonal to the major axis direction of the liquid crystal at the emerging end of the first body. Moreover, an incident light having a polarizing direction parallel to a major axis direction of the liquid crystal of the first liquid crystal body is subjected to an effect due to extraordinary ray refractive index of the liquid crystal in the first body, and is subjected to an effect due to ordinary ray refractive index in the second liquid crystal body, in which the major axis direction of the liquid crystal is orthogonal to the major axis direction of the first body. In this case, if the first body and the second body are substantially of the same construction, the difference of focus positions due to the polarizing direction becomes negligible amount. While in the voltage applying condition, the liquid crystal molecular structure is aligned parallel to the optical axis, so that whole incident light flux are subjected to an effect due to ordinary ray refractive index of the liquid crystal and transmitted through the first body and the second body.

The above constructed imaging optical system according to the present invention does not require the function of selecting the polarizing directions for preventing generation of a double image, so that it is possible to obtain an endoscope having a variable focusing function with substantially 100% transmittance both in the far point infocusing condition and in near point infocusing condition.

Particularly, in the micro-optical system, such as an endoscope, the focal length of optical system itself is short, and the diameter of light flux is short, so that in order to load the variable focus liquid crystal lens, the thickness of the liquid crystal may be made thin. Therefore, according to the present invention, it is possible to obtain a variable focus lens with high response speed, high contrast and high transmittance. Moreover, the current endoscope requires high operationally, low invasiveness, and high compaction.

If the driving system is an electrical system, therefore, it is preferably compacted that the variable focus liquid crystal lens improves responsibility and contrast property, as the objective system is compacted, thereby imposing the variable focusing function to the endoscope or the like.

Then, if the variable focusing lens is loaded on the endoscope, the following constituent factors to obtain the same lens power for whole polarized light without a plarizer and to obtain sufficient lens power variation and the sufficient response speed as an endoscope, are explained hereinafter.

In order to obtain the same lens power for whole polarized light without arising the double image, as described above, the polarized components incident on the first liquid crystal body as extraordinary ray and the polarized components incident on the first liquid crystal body as ordinary ray must have the same lens power received from the above member. On working and assembling the endoscope, when the first body and the second body have the same liquid crystal material, assuming that the radius curvatures of the front face of the first body, the rear face of the first body, the front face of the second body and the rear face of the second body have the radius curvatures $R_1$, $R_1'$, $R_2$, $R_2'$, respectively, and have birefringence n, $n_o$ and $n_e$, respectively, and the distance between the first body and the second body is very short, respective radius curvature have to satisfy following equation.

$$(n_e-n)/R_1+(n-n_e)/R_1'+(n_o-n)/R_2+(n-n_o)/R_2'=(n_o-n)/R_1+(n-n_o)/R_1'+(n_e-n)/R_2+(n-n_e)/R_2' \quad (1)$$

From the above equation, respective radius curvature have to satisfy following relation.

$$1/R_1-1/R_1'-1/R_2+1/R_2'=0 \quad (2)$$

When the conditions that equation (2) is satisfied and easiness on working and assembling is obtained, are considered, it is desired that the first and the second bodies have a shape substantially symmetrical to a plane perpendicular to the optical axis.

The substantially symmetrical shape of the first body and the second body is a curved surface, and these curved surfaces are displaced opposite to each other.

A substrate in which the first body and the second body are filled in, is formed by a plate, a biconcave lens and a plane lens.

A distance $L_{12}$ between the first body and the second body satisfies following equation:

$$0.1 \text{ (mm)} \leq L_{12} \leq 0.4 \text{ (mm)}. \quad (3)$$

It is ideal to make the distance $L_{12}$ being 0 in order to prevent a double image from being caused, and desirable to make the distance being at least 0.4 (mm). In this case, the amount of the distance $L_{12}$ has a limitation on working, so that if the distance has not more than lower limit 0.1 (mm), the working becomes hard, and if the distance has not less than upper limit 0.4 (mm), the double image is caused, and thus resolution of the image becomes deteriorated.

The thickness d of the first body and the second body, an absolute value $|R|$ of radius curvature of the first body and the second body, and the diameter D of an aperture diaphragm of the first body and the second body satisfy the following relation:

$$D^2 8 \cdot |R| \leq d \leq 0.04 \text{ (mm)}. \quad (4)$$

If the thickness d of the first and second bodies exceeds the upper limit 0.04 (mm), the response speed becomes slow, and it is not desirable. Particularly, the current main flow of the endoscope is an electronic scope, considering that the feature of driving the lens during one frame scanning is performed by using a liquid crystal having the birefringence difference Δn=0.2, it is necessary to set the thickness d of the liquid crystal to d≦0.01 (mm). The more increase of thickness of liquid crystal, the less contrast and transmittance of the image, so that it is not preferable to increase the thickness of the liquid crystal. In this case, the lower limit of the thickness d is limited by the diameter D of the light flux, so that if the condition $D^2/8 \cdot |R| \leq d$ is not satisfied, necessary light flux is subjected to a shading or eclipse. Therefore, the thickness d has to satisfy the above equation (4).

The absolute value $|R|$ of radius curvature of the first body and the second body satisfies following relation:

$$1 \text{ (mm)} \leq |R| \leq 80 \text{ (mm)}. \quad (5)$$

On considering that the smaller the birefringence difference Δn, the smaller the viscosity of the liquid crystal, and thus the faster the response speed, it is desirable to satisfy the relation $|R| \leq 80$ (mm). In this case, as shown in the equation (4), the feature of decreasing the radius curvature of the substrate in which the first and the second liquid crystal bodies are enclosed, is that the thickness d of the first and the second bodies is made thick. That is, The smaller the radius curvature, the thicker the liquid crystal layer. It becomes a cause of deteriorating the response speed, the contrast and the transmittance of the liquid crystal. Therefore, it is preferable to satisfy the relation $|R| \geq 1$ (mm).

The birefringence difference Δn of the liquid crystal of the first body and the second body satisfies following relation:

$$0.15 \leq \Delta n \leq 0.35. \quad (6)$$

The larger the birefringence difference Δn, the larger the radius curvature R in order to obtain necessary lens power, so that as shown in the equation (4), the thickness of the first and the second bodies can preferably be made small. Therefore, it is preferable to satisfy the relation 0.15≦Δn. In this case, the material of large birefringence difference Δn has high viscosity, thereby deteriorating the response speed. Therefore, it is preferable to satisfy the equation (6). If the birefringence difference Δn exceeds the upper limit of the equation (6), the response becomes slow because of viscosity of the material. If the birefringence difference Δn is less than the lower limit, the liquid crystal becomes thick in order to obtain necessary lens power, thereby deteriorating the response speed, the contrast and the transmittance of the liquid crystal.

The birefringence difference Δn of the liquid crystal and the absolute value $|R|$ of radius curvature of the first body and the second body satisfy following relation:

$$0.005 \leq \Delta n/|R| \leq 0.1. \quad (7)$$

On considering the condition that necessary lens power is made variable, the amount ΔΦ of lens power variation caused by the variable focusing is shown in following equation, in which $n_o$ is an ordinary ray refractive index of liquid crystal, $n_e$ is an extraordinary refractive index, and $\Delta n$ is birefringence difference.

$$\Delta\Phi = \Delta n/R - \Delta n(n_o-n)R^2 \qquad (8)$$

The effective amount $\Delta\Phi$ of lens power variation as an endoscope have to satisfy a following relation to the lens power $\Phi$ of the imaging lens.

$$0.005 \leq \Delta\Phi/\Phi \qquad (9)$$

Particularly, it is most desirable that $\Delta\Phi/\Phi$ is made 0.01 or so. However, if $\Delta\Phi$ is too large, when liquid crystal lens is used as a two focus switching lens, the focusing depth of near point side and the focusing depth of far point are not superimposed, thereby arising an unobserved region. Therefore, it is desirable for the equation (9) to satisfy following equation.

$$0.005 \leq \Delta\Phi/\Phi \leq 0.1 \qquad (10)$$

A distance L between the optical member and the aperture diaphragm and a focal length f of whole imaging optical system satisfy following relation:

$$L \leq f/2. \qquad (11)$$

The imaging optical system is a retrofocus type.

An outer diameter of the optical member is less than $\Phi 5$ mm.

It is effective as an endoscope lens and in order to make the liquid crystal layer thin, it is preferable to make the diameter $\Phi$ of lens 5 mm or less.

The substrate filling the first body and the second body therein is constructed by an infrared ray cutting filter.

In the case of the endoscope, the spectral photosensitivity for infrared ray of a solid state imaging element is high, so that it is necessary to arrange a filter having an infrared ray cutting function. Then, the substrate of the liquid crystal lens is formed by the infrared ray cutting filter, resulting in a possibility of a space saving. Moreover, the first liquid crystal body and the second liquid crystal body are made homogeneous alignment, respectively, and the voltage applied to the liquid crystal is continuously changed, so that the focal length can also be changed.

In second aspect of the imaging optical system according to the present invention, there is provided an imaging optical system comprising an optical member including a first body consisting of a substantially transparent birefringent liquid crystal member, a second body consisting of a substantially transparent birefringent liquid crystal member, and at least a pair of electrodes for adding an electric field or a magnetic field onto the first body and the second body, a rear face of the first body being aligned perpendicular to a front face of the second body, and a distance L between the optical member and an aperture diaphragm and a focal length f of whole imaging optical system satisfy following relation:

$$L \leq f/2. \qquad (11)$$

As an objective lens of endoscope or the like, generally, there is a lens of a retrofocus type, in which a slant incident on the liquid crystal lens is decreased as the lens is near the aperture diaphragm. Therefore, the displacement of the liquid crystal lens near the aperture diaphragm means that the total image run-out and the coloring caused by birefringence in the liquid crystal are decreased. Moreover, the diameter of the light flux becomes small as accessed to the aperture diaphragm, so that effective aperture can be made small, and thus the thickness of the liquid crystal layer can also be suppressed. Therefore, the focal length f of whole imaging lens system and the distance L between the aperture diaphragm and the liquid crystal lens have to satisfy the above relation of equation (11).

If the distance L exceeds the upper limit of the equation (11), the total image run-out, the coloring caused and the deterioration of the response speed are caused. Therefore, it is necessary to arrange the liquid crystal lens before and after the aperture diaphragm.

The member is placed before or after an aperture diaphragm.

The first body and the second body have substantially symmetrical shape against a plane perpendicular to an optical axis, the substantially symmetrical shape of the first body and the second body is a curved surface, and these curved surfaces are displaced opposite to each other.

The absolute value $|R|$ of radius curvature of the first body and the second body satisfies following relation:

$$1 \text{ (mm)} \leq |R| \leq 80 \text{ (mm)}. \qquad (5)$$

A distance $L_{12}$ between the first body and the second body satisfies following relation:

$$0.1 \text{ (mm)} \leq L_{12} \leq 0.4 \text{ (mm)}. \qquad (3)$$

Assuming that the thickness of the first body and second body is d, an absolute value of radius curvature of the first body and the second body is $|R|$, and an aperture diaphragm radius of the first body and the second body is D, the following relation is satisfied:

$$D^2/8|R| \leq d \leq 0.04 \text{ (mm)}. \qquad (4)$$

The difference of birefringence $\Delta n$ of the liquid crystal of the first body and the second body satisfies following relation:

$$0.15 \leq \Delta n \leq 0.35. \qquad (6)$$

In third aspect of the imaging optical system according to the present invention, there is provided an imaging optical system comprising an optical member including a first body consisting of a substantially transparent birefringent liquid crystal member, a second body consisting of a substantially transparent birefringent liquid crystal member, and at least a pair of electrodes for adding an electric field or a magnetic field onto the first body and the second body, a front face of the first body being aligned perpendicular to a rear face of the second body, rear face of the first body and the front face of the second body are made a curved surface, and these curved surfaces are displaced opposite to each other.

According to the present invention, the imaging optical system comprises an optical member including a first body consisting of a substantially transparent birefringent liquid crystal member, a second body consisting of a substantially transparent birefringent liquid crystal member, and at least a pair of electrodes for adding an electric field or magnetic field onto the first body and the second body, a front face of the first body being aligned perpendicular to a rear face of the second body, so that if such an imaging optical system is loaded as an imaging optical system for an endoscope, a variable focusing function can be added to the endoscope without any requiring a polarizing plate.

The position setting the first body and the position setting the second body are, in fact, shifted more or less in the imaging system, the total image run-out due to the polarizing direction is slightly caused in accordance with the height difference of ray incident on the first and the second bodies. In order to make this total image run-out minimum, it is necessary to make the positional shift of the plane contributing the lens power variation small as soon as possible by arranging the curved surfaces of the first and the second bodies opposite to each other. Concretely, the substrate for enclosing and sealing the liquid crystal is formed by laminating a plate, biconcave lens and plane lens, in turn, and then, the first body and second liquid crystal bodies are sealed in the void portions formed thereamong. This method has a high effect of preventing double focus by accessing refraction surfaces to each other, and the role in which the aligning directions of the first and second bodies are arranged perpendicular to each other, can be performed by only one biconcave lens, so that an assembling step can be improved.

Assuming that the thickness of the first body and the second body is d, an absolute value of radius curvature of the first body and the second body is $|R|$, and an aperture diaphragm radius of the first body and the second body is D, the following relation is satisfied:

$$D^2/8|R| \leq d \leq 0.04 \text{ (mm)}. \tag{4}$$

The absolute value $|R|$ of radius curvature of the first body and the second body satisfies following relation $$1 \text{ (mm)} \leq |R| \leq 80 \text{ (mm)}. \tag{5}$$

An imaging optical system comprises a member including a first body consisting of a substantially transparent birefringent liquid crystal member, a second body consisting of a substantially transparent birefringent liquid crystal member, and at least a pair of electrodes for adding an electric field or a magnetic field onto the first body and the second body, a rear face of the first body being aligned perpendicular to a front face of the second body, and a distance L12 between the first body and the second body satisfies following relation:

$$0.1 \text{ (mm)} \leq L_{12} \leq 0.4 \text{ (mm)}. \tag{3}$$

The first body and the second body have an asymmetric shape to a surface perpendicular to an optical axis.

The absolute values $|R_1|$, $|R_2|$ of radius curvature of the first body and the second body satisfy following relation:

$$0.5 \leq |R_1/R_2| \leq 2. \tag{12}$$

In order to prevent a generation of double image, as described above, two liquid crystal layers having its curvature being varied more or less are arranged in the asymmetric form to a plane perpendicular to the optical axis, instead of in the symmetric form, thereby obtaining an effect of correcting the shift of positions of the first and the second bodies, resulting in a possibility of decreasing the arise of double image. In this case, the absolute values $|R_1|$, $|R_2|$ of radius curvature of the first body and the second body have to satisfy the above equation (12).

The absolute value $|R|$ of radius curvature of the first body and the second body satisfies following relation:

$$1 \text{ (mm)} \leq |R| \leq 80 \text{ (mm)}. \tag{5}$$

An imaging optical system comprises an optical member including a first body consisting of a substantially transparent birefringent liquid crystal member, a second body consisting of a substantially transparent birefringent liquid crystal member, and at least a pair of electrodes for adding an electric field or a magnetic field onto the first body and the second body, a rear face of the first body being aligned perpendicular to a front face of the second body, the absolute value $|R|$ of radius curvature of the first body and the second body satisfies following relation:

$$|R| \leq 150 \text{ (mm)}. \tag{13}$$

On considering the limit of general birefringent index difference $\Delta n$ being about 0.3, the absolute value $|R|$ of radius curvature have to satisfy the above equation (13).

The absolute value $|R|$ of radius curvature of the first body and the second body satisfies following relation:

$$1 \text{ (mm)} \leq |R| \leq 80 \text{ (mm)}. \tag{5}$$

The first body and the second body have a plane and curved surfaces, and the absolute value $|R|$ of radius curvature of the first body and the second body satisfies following relation:

$$1 \text{ (mm)} \leq |R| \leq 40 \text{ (mm)}. \tag{14}$$

If the first and the second liquid crystal bodies have the plane and curved surfaces, the above absolute value $|R|$ have to satisfy the equation (14) in order to make the working easy.

An imaging optical system comprises an optical member including a first body consisting of a substantially transparent birefringent liquid crystal member, a second body consisting of a substantially transparent birefringent liquid crystal member, and at least a pair of electrodes for adding an electric field or a magnetic field onto the first body and the second body, a rear face of the first body being aligned perpendicular to a front face of the second body, and assuming that the thickness of the first body and the second body is d, an absolute value of radius curvature of the first body and the second body is $|R|$, and an aperture diaphragm radius of the first body and the second body is D, the following relation is satisfied:

$$D^2/8|R| \leq d \leq 0.4 \text{ (mm)}. \tag{4}$$

An imaging optical system comprises an optical member including a first body consisting of a substantially transparent birefringent liquid crystal member, a second body consisting of a substantially transparent birefringent liquid crystal member, and at least a pair of electrodes for adding an electric field or a magnetic field onto the first body and the second body, a rear face of the first body being aligned perpendicular to a front face of the second body, and the difference of birefringence Δn of the first body and the second body satisfies following relation:

$$0.15 \leq \Delta n \leq 0.35. \quad (6)$$

In case of using the endoscope, also, the lens is made accessed to the subject in far point infocusing condition, and the pint of the lens is switched in the near point infocusing condition at a point that the lens is accessed to the subject to some extent, after which the subject is observed in the near infocusing condition. When the object position for performing the pint switching from the near point infocusing condition to far point infocusing condition and the object position for performing the pint change from the far point infocusing condition to near point infocusing condition, are positioned near to each other, if the object is present near the object switching position, even the object is moved slightly back and forth, the pint switching is performed frequently. Therefore, in case of loading a lens utilizing a liquid crystal on an imaging optical system to consider the adding of a variable focusing function, the liquid crystal having large birefringence must be utilized in order to obtain a change of lens power. However, the liquid crystal having large birefringence has high viscosity and slow response speed, so that it is difficult to obtain sharp image in case of performing pint switching frequently.

As a countermeasure of this problem, an imaging optical system capable of always obtaining sharp image by preventing the pint switching from being performed frequently more than requirable, when the object position is near the pint switching position, may be obtained. In this case, an imaging optical system comprises a pint switching means and a means having an auto-focusing function for setting an object position performing a pint switching from the far point infocusing condition to near point infocusing condition, and an object position performing a pint switching from the near point infocusing condition to far point infocusing condition, to different position.

An imaging optical system further comprises a means having a function for detecting the above object position.

Concretely, the object position xb performing a pint switching from the far point infocusing condition to near point infocusing condition and the object position Xb performing a pint switching from the near point infocusing condition to far point infocusing condition, are set to different position to each other, and even the object is moved back and forward more or less near the switching position after once performing the pint switching, the pint switching does not perform more than requirable, and then in case of moving the object back and forward largely, the pint switching is performed, so that the sharp image can always obtained irrespective of the response speed of the liquid crystal.

In order to observe the object up to near point side of the near point infocusing condition, the relation between the object position Xb and the object position xb have to satisfy following relation:

$$xb \leq Xb. \quad (15)$$

On considering the focal depth required to the endoscope, the object positions xb and Xb have to satisfy following relation:

$$1 \text{ (mm)} \leq Xb-xb \leq 25 \text{ (mm)}. \quad (16)$$

The pint switching position from the far point infocusing condition to near point infocusing condition is set to an object point distance under the near point infocusing condition, and the pint switching position from the near point infocusing condition to far point infocusing condition to different position is set to an object point distance under the far point infocusing condition.

The object position xb is set to the best object position under the near point infocusing condition and the object position Xb is set to the best object position under the far point infocusing condition, so that sharp image can be obtained even at the time of pint switching.

The pint switching means is constructed from a material having an electro-optical effect such as a liquid crystal or the like.

BRIEF DESCRIPTION OF THE DRAWINGS

FIG. 9 is an explanatory view defining radius of curvature of respective optical elements and its surface intervals in the fourth embodiment of the present invention; and FIG. 10 is a perspective view showing a construction of a distal section A of the endoscope shown in respective embodiments.

DETAILED DESCRIPTION OF THE PREFERRED EMBODIMENT

Figure 1:
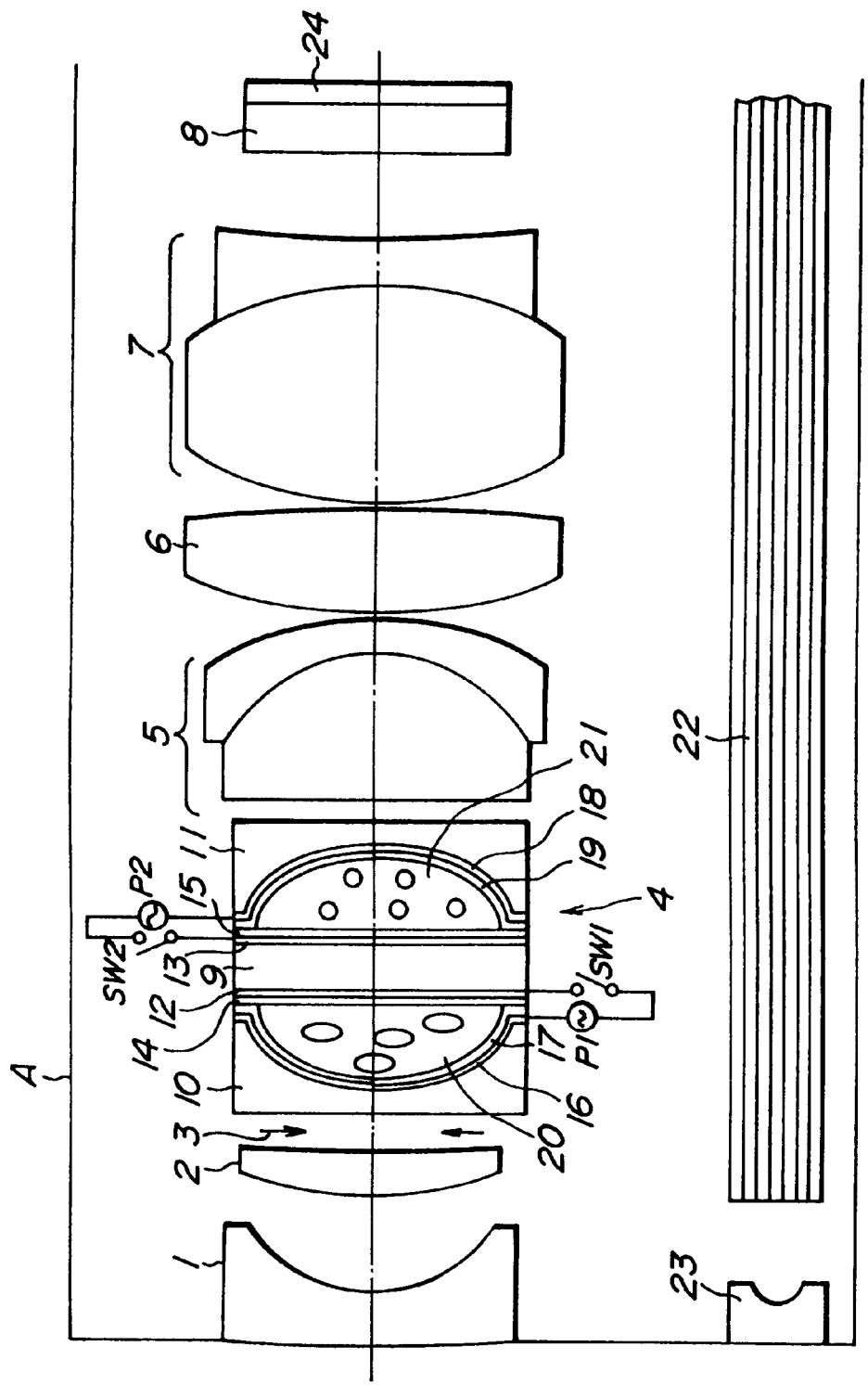
FIG. 1 is an explanatory view showing a construction of first embodiment of an imaging optical system according to the present invention.

Now to the drawings, there are shown various embodiments of an imaging optical system according to the present invention. Like parts are shown by corresponding reference characters throughout several views of the drawings.

FIG. 1 shows a construction of first embodiment of an imaging optical system according to the present invention, which is constructed as an imaging optical system for electron endoscope.

An end face of a distant section A of the endoscope shown in FIG. 1 is provided with a concave lens 1 which also serves as a cover glass, after which, along its optical axis, there are arranged a lens 2, an aperture diaphragm 3, a liquid crystal lens 4, a lens 5 of two lens elements, a lens 6, a lens 7 of two lens elements, a cover glass 8 for a solid state imaging element, and a CCD 24 (charge coupled device) as the solid state imaging element, in the order given. The liquid crystal lens 4 is so formed that liquid crystal members are bisymmetric with respect to a plane-parallel plate lens 9.

That is, the shown left portion of the liquid crystal lens 4 comprises the plane-parallel plate lens 9, a plano-concave lens 10, a transparent electrode 12 and an aligned film 14 which are covered in turn on a left end face of the plane-parallel plate lens 9, a transparent electrode 16 and an aligned film 17 which are covered in turn on a concave surface of the plano-concave lens 10, and a nematic liquid crystal 20 filled in a concave lens shaped void (sell) formed between the left end face of the plane-parallel plate lens 9 and the concave surface of the plano-concave lens 10. Similarly, the shown right portion of the liquid crystal lens 4 comprises the plane-parallel plate lens 9, a plano-concave lens 11, a transparent electrode 13 and an aligned film 15 which are covered in turn on a right end face of the plane-parallel plate lens 9, a transparent electrode 18 and an aligned film 19 which are covered in turn on the concave surface of the plano-concave lens 11, and a nematic liquid crystal 21 filled in a concave lens shaped void (cell) formed between the right end face of the plane-parallel plate lens 9 and the concave surface of the plano-concave lens 11. The above aligned films 14 and 15 are displaced in the orthogonal directions to each other, the transparent electrodes 12, 16; 13, 18 are connected to alternating supply sources P1, P2, (for example 50 Hz) through switches SW1, SW2, respectively. In this case, the aligned films 14 and 15 may be arranged in the directions orthogonal to each other, but it is preferable to set the aligned directions in parallel to each other, in order to change focal length successively.

An illuminating optical system consisting of a light guide 22 and an illuminating lens 23 is disposed on the above distant section A of the endoscope in parallel to the imaging optical system.

In this embodiment, as shown in FIG. 1, if the switches SW1, SW2 are made OFF condition, the nematic liquid crystals 20, 21 in the liquid crystal lens 4 become a homogeneous structure or alignment, that is, the major axis direction of the liquid crystalline molecule becomes an alignment orthogonal to an optical axis. In this case, the incident light from an object having a polarizing direction perpendicular to the aligned film 17 is subjected to a function due to an ordinary ray refractive index of the liquid crystal 20, rotated therein, and passed in the liquid crystal 21 through the aligned films 14, 15 having a polarizing direction orthogonal to each other. In this case, this incident light is subjected to a function due to an extraordinary ray refractive index of the liquid crystal 21, and passed therein, since the polarizing direction of the light and the major axis direction of the liquid crystal are coincident in the liquid crystal 21. While, the incident light having polarizing direction parallel to the aligned film 17 is, in the liquid crystal 20, subjected to the function due to the extraordinary ray refractive index of the liquid crystal 20 and passed therethrough, and also is, in the liquid crystal 21, subjected to the function due to the ordinary ray refractive index of the liquid crystal 21 and passed therethrough, in accordance with the above principle. In this case, the liquid crystals 20, 21 are enclosed in the plano-convex lenses 10 and 11 having equal absolute values and curvature of reverse signs, respectively, so that the liquid crystal lens 4 acts as a lens having a substantially the same refractive function to the full polarizing component of incident light flux.

Figure 2:
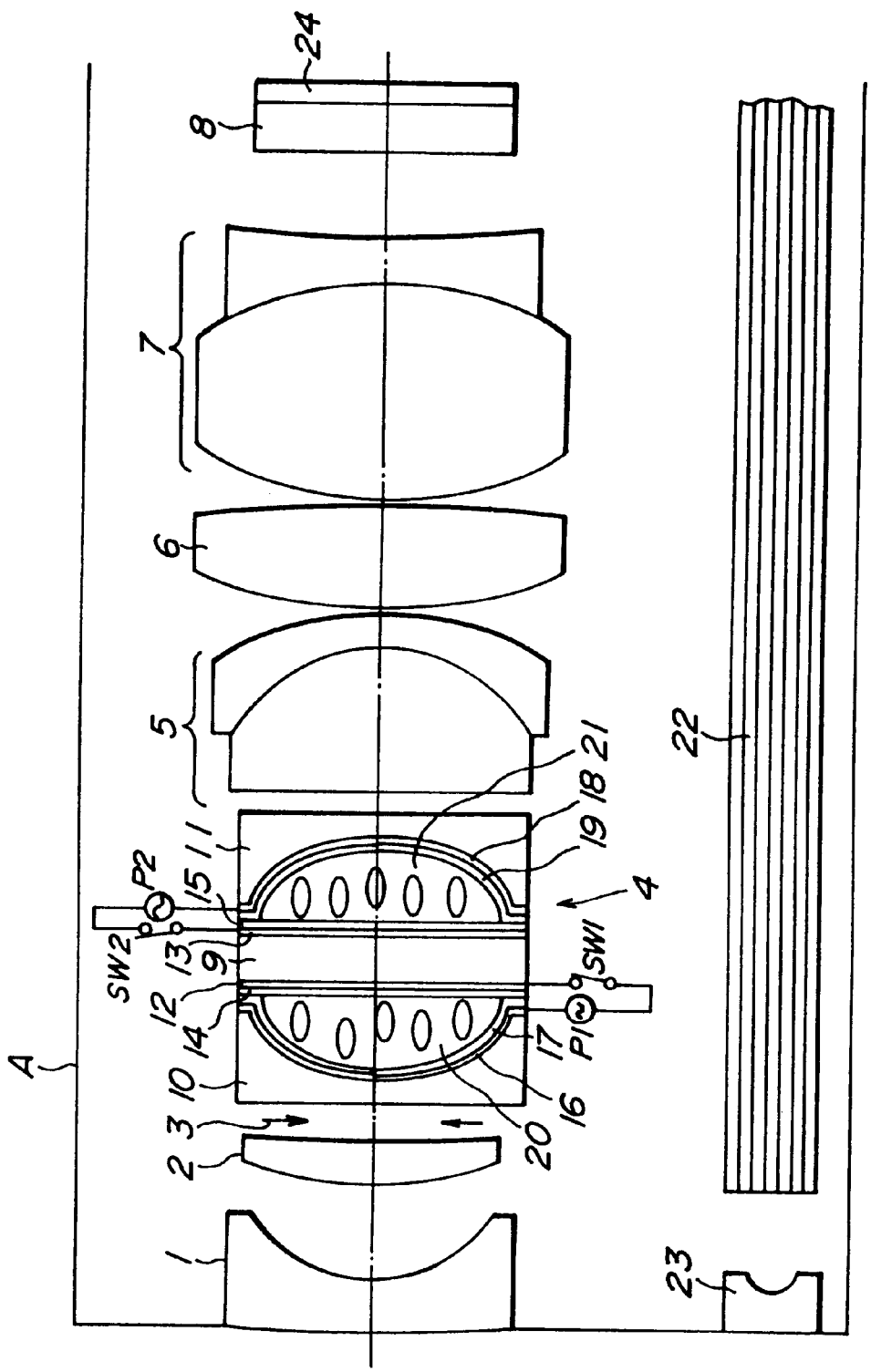
FIG. 2 is an explanatory view showing condition of applying voltage on liquid crystal in the first embodiment.

While as shown in FIG. 2, if the alternating voltage is applied by making the switches SW1, SW2 ON state, the nematic liquid crystals 20, 21 in the liquid crystal lens 4 become a homeotropic structure or alignment, that is, the major axis direction of the liquid crystalline molecule becomes an alignment parallel to an optical axis. Therefore, the whole light incident on the liquid crystals 20, 21 are subjected to the function due to ordinary ray refractive index of the liquid crystals 20, 21 and transmitted through the liquid crystal lens 4.

The above liquid crystals 20, 21 have a bisymmetric shape for the plane-parallel lens 9 in order to obtain the same lens power in whole polarizing directions. For example, by using a concave lens having an absolute value $|R|$ of radius curvature R of 27 mm and a liquid crystal having a birefringence difference $\Delta n$ of 0.24, and by using a distance between the plane-parallel plate lens 10 and the plane-parallel plate lens 11 being a value from 0.1 mm to 0.4 mm (for example, 0.3 mm), a best object position can be changed from 8 mm to 18 mm. Moreover, the thickness of respective liquid crystals may be set to 20 $\mu$m by setting the liquid crystal lens 4 at the position of 0.15 mm after the aperture diaphragm 3, thereby improving the response speed.

In the present embodiment, the thickness of and the distance between the liquid crystal 20 and 21 of the liquid crystal lens 4, are set as described above, thereby preventing total image run-out due to polarizing direction, resulting in a possibility of suppressing run-out of the image on the end face of CCD 24 less than 3 $\mu$m. This run-out amount of the image is an amount of image run-out which can be ignored in case of considering sampling frequency of CCD. The liquid crystal 4 can be wired in a driving section without substantially occupying the space, by providing the electrodes on a D cutting portion provided on its side surface, because of the thickness of 1 mm or the like, so that the liquid crystal can be loaded without substantially changing the shape of the distal portion of the endoscope in the diametrical and longitudinal directions.

In the above descriptions, as a method of forming the aligned film for aligning the liquid crystals 20, 21, there can be utilized a method of rubbing an applied polyimide film, or a method of rhombic vaporizing silicon oxide. The method of forming the aligned film by the rhombic vaporizing can form a homogeneous and contactless uniform aligned film for a lens having minimized and curved surface as in this embodiment, so that it is preferable to obtain an objective lens for endoscope. Moreover, $S_iO_2$ is coated between the glass material and the ITO film as a transparent electrode, so that alkaline component included in the glass material can be prevented from being flew out. In this case, in order to prevent a reflection at a boundary between the lens and the liquid crystal, it is desirable to hold the following relationship for the thickness of $S_iO_2$, ITO and polyimide, ds, di and dp:

$$10 \text{ (nm)} \leq ds \leq 50 \text{ (nm)} \tag{17}$$

$$80 \text{ (nm)} \leq di \leq 150 \text{ (nm)} \tag{18}$$

$$19 \text{ (nm)} \leq dp \leq 50 \text{ (nm)} \tag{19}$$

Sealing of liquid crystal is performed by forming a wall outside effective aperture of the lens with epoxy resin, in which spacers are inlaid, by pouring liquid crystals after providing substrate, and by sealing the injection inlet. In this case, the spacer has an insulating effect, in the same manner as the aligned film, so that on considering injection of the liquid crystal, it is desirable to utilize a ball shaped spacer of 4 $\mu$m or more. In this case, only considering two focus switching, if the liquid crystal is made a twistnematic structure, in order to make the polarized light incident on the liquid crystal rotated by 90 degree in the liquid crystal without depending the thickness of the liquid crystal to some extent. In the present embodiment, in order to make the incident light on the liquid crystal transmitted by rotating the polarized surface more than 95%, it is necessary to make the thickness of the liquid crystal more than 6 μm. In this case, on considering the thickness of the liquid crystal at the center of the lens, the increase of the spacer more than requirable makes the response speed slow.

As to the drive of the liquid crystal, it is desirable to drive the liquid crystal at an alternating field with the frequency of more than 50 Hz, and in case of considering increase of response speed, it is desirable to drive the liquid crystal with the frequency having largely variable relative permittivity (for example, high frequency of 1 kHz or more). Moreover, the voltage at the near point is set to about 1 V, instead of applying no voltage, thereby improving the response speed more. This embodiment utilizes the liquid crystal having positive anisotropy of dielectric constant, but negative anisotropy of dielectric constant may be utilized, instead thereof, so that this makes the liquid crystal homogeneous structure at the application of voltage, and makes the liquid crystal homeotropic structure at the application of no voltage. In this case, the liquid crystal is driven only in the observation of near point side. Moreover, in utilizing, if the liquid crystal adequately operates with two focus switchings of near point side and far point side, the liquid crystal may be operated with TN (twist nematic) structure. In this case, the alignment of liquid crystal at the application of no voltage is stabilized, and thus more sharp image can be obtained. Even in this case, it is necessary to make the alignment at both concave surface perpendicular to each other.

Moreover, the pint can be switched in accordance with the object point distance by providing a function of detecting the object point distance (the distance up to object position) based on catoptric light intensity from the object in self illuminating light such as trigonometric range finding method, image phase difference method or light guide and the like. In this case, the object position performing a pint switching from the far point infocusing condition to near point infocusing condition and the object position performing a pint switching from the near point infocusing condition to far point infocusing condition, are set to different position to each other, thereby preventing the pint switching from being caused frequently in case of presenting the object near the pint switching position, resulting in an acquirement of permanent sharp image. Particularly, the object position performing a pint switching from the far point infocusing condition to near point infocusing condition is set to a best switching position at the side of the near point infocusing condition (for example, 8 mm), and the object position performing a pint switching from the near point infocusing condition to far point infocusing condition is set to a best switching position at the side of the far point infocusing condition (for example, 18 mm), thereby decreasing frequency of pint switching from the far point infocusing condition to near point infocusing condition, resulting in an acquirement of permanent sharp image.

The imaging optical system according to the present embodiment has preferable conditions in case of being constructed as an imaging optical system for an electric endoscope which are as follows.

In the optical system having wide angle of view, such as an objective lens for the endoscope, an optical system of retrofocus type, in which back focus is also taken, is commonly used. Since in order to prevent the solid state imaging element from being photosensitized with infrared radiation, it is necessary to displace a filter having a function of cutting the infrared radiation. Then, if a substrate for constructing the liquid crystal lens is constructed by an infrared ray cutting filter, the liquid crystal lens can be arranged without newly providing a space for the lens.

Moreover, if the incident light for the liquid crystal lens is largely slanted to the optical axis, there is a cause for a double image or a coloring by ghost in the liquid crystal thereby. Then, as in the present embodiment, it is desirable to displace the liquid crystal near the aperture diaphragm, particularly, front or rear of the aperture diaphragm.

In the imaging optical system requiring a lens having small diameter, such as an endoscope, also, it is required for the liquid crystal lens to make the diameter of the liquid crystal small to some extent, so that the outer diameter φ of the liquid crystal 5 must be made lower than 5 mm.

Moreover, the thickness of the liquid crystal 20 and 21 must be made lower 0.05 mm by considering a scatter and absorption of the light for the liquid crystal into effect, and in the minimized lens for use in the endoscope, the absolute value |R| of the radius of curvature R of the plano-concave lens 10 and 11 must be made more than 1 mm and lower than 150 mm.

In this embodiment, moreover, as liquid crystals 20 and 21, there is used a liquid crystal having a birefringent difference Δn of the nematic liquid crystal being 0.24, but this birefringent difference Δn is a value corresponding to a focus variation amount of the liquid crystal lens 4, so that it is required to make the birefringent difference Δn of the nematic liquid crystal larger than 0.15 and smaller than 0.35, in order to obtain the variation of the focal length required for an endoscope.

If the distance d between the liquid crystals 20 and 21 is large, slight difference is caused in the light path of the liquid crystal lens due to the polarizing direction, resulting in a cause of generating the double image, so that the distance d between the liquid crystal lenses 20 and 21 must be made more than 0.1 mm and less than 0.4 mm.

Figure 3:
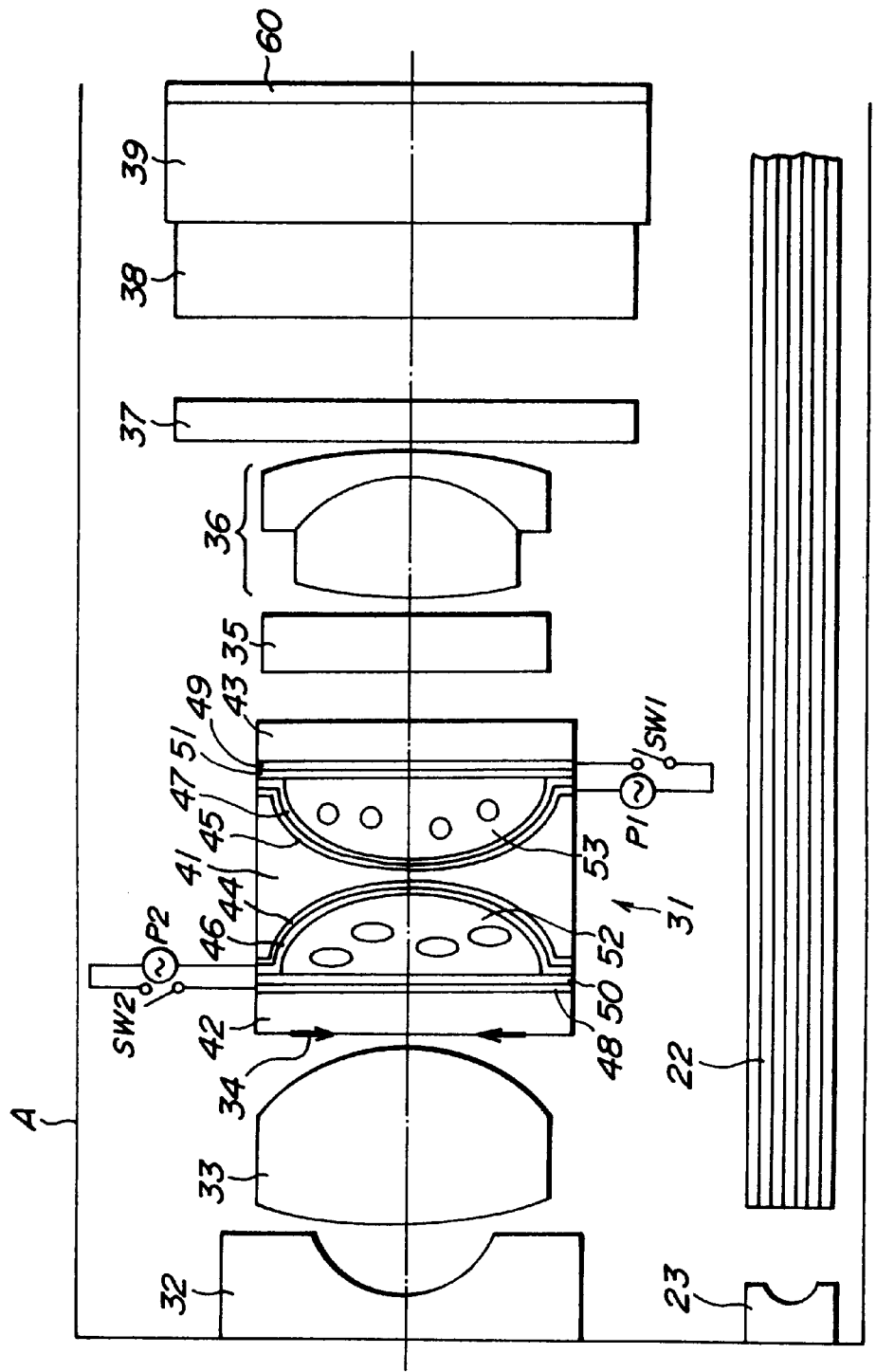
FIG. 3 is an explanatory view showing a construction of second embodiment of an imaging optical system according to the present invention.
Figure 4:
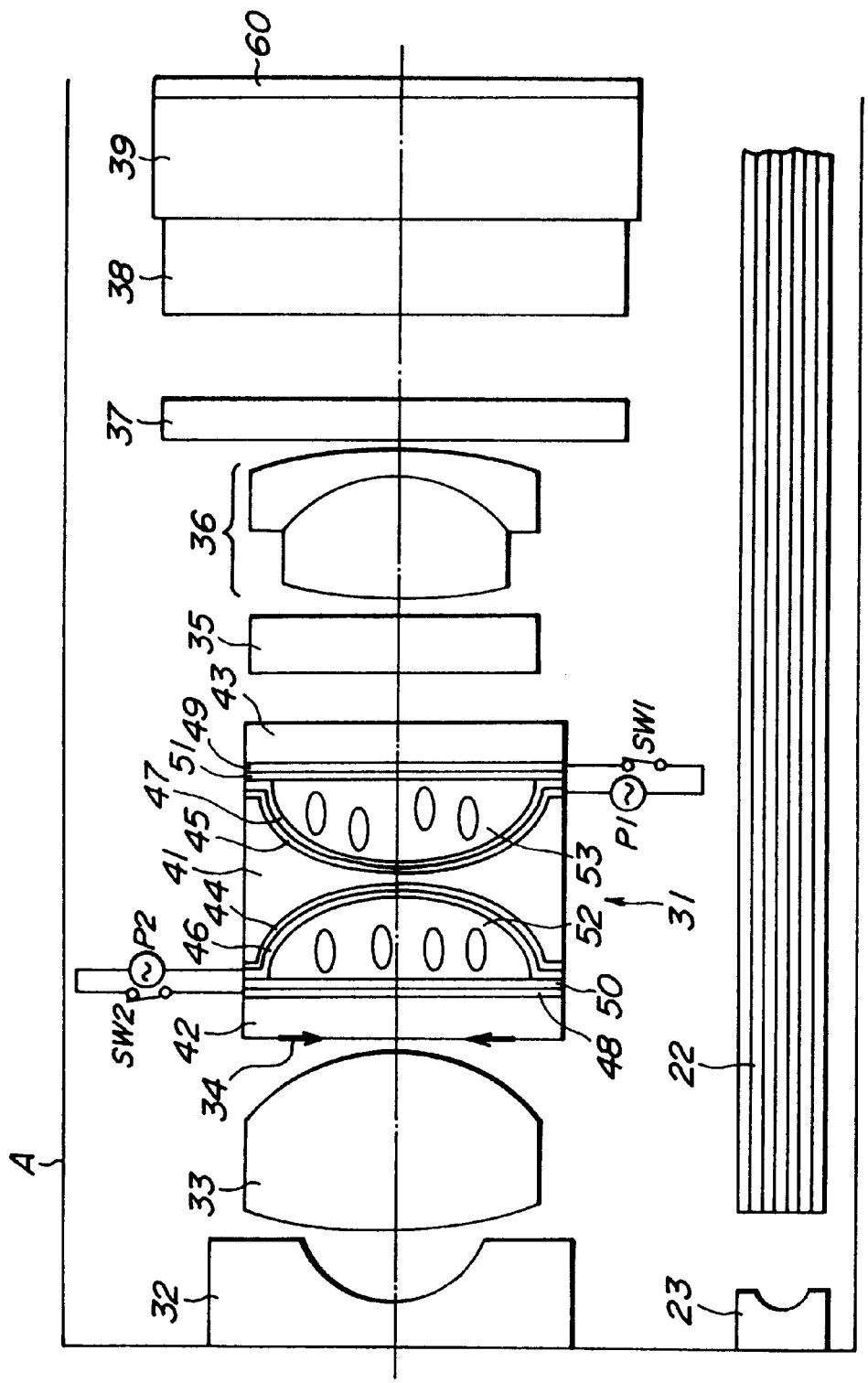
FIG. 4 is an explanatory view showing condition of applying voltage on liquid crystal in the second embodiment.

FIGS. 3 and 4 show a construction of second embodiment of an imaging optical system according to the present invention, particularly, FIG. 3 shows the condition in which a voltage is not applied to the liquid crystal, and FIG. 4 shows the condition in which a voltage is applied to the liquid crystal. The image optical system of the second embodiment is intended to load on an endoscope for digestive organs. A liquid crystal 31 of this embodiment comprises a bi-concave lens 41 and two plane-parallel plate lenses 44, 45 and the other optical system (optical elements 32 38) of this embodiment are the same construction as in the first embodiment. In this embodiment, also, a solid state imaging element (CCD) 60 is disposed after a cover glass 39 for the solid state imaging element and an image is focused on the end surface of the CCD.

The both surfaces of the bi-concave lens 41 of the liquid crystal 31 are covered with transparent electrodes 44, 45 and aligned films 46, 47 disposed in the directions orthogonal to each other, in turn, respectively, and the surfaces at the side of the bi-concave lens, of the plane-parallel plate lenses 42, 43 are covered with transparent electrodes 48, 49 and aligned films 50, 51, respectively. Nematic liquid crystals 52, 53 are enclosed and sealed, respectively, in a concave lens shaped space (sell) formed by covered films of the bi-concave lens 41 and the plane-parallel plate lenses 42, 43 disposed so as to opposite to the both surfaces, respectively. The transparent electrodes 45, 49 and 44, 48 are connected to alternating supply sources P1, P2 (for example, 50 Hz, 10 V) through switches SW1, SW2, respectively, in the same manner as the first embodiment.

The distal section A of the endoscope is provided with an illuminating optical system consisting of a light guide 22 and an illuminating lens 23 in parallel to the imaging optical system. By constructing the liquid crystal lens 31 with the use of the above bi-concave lens 41, the distance or interval between the liquid crystals 52 and 53 can be made narrow rather than the case of the first embodiment in which the liquid crystal is disposed on the both sides of the plane-parallel plate, thereby decreasing the double image (total image run-out) caused by the difference of the polarizing direction.

Figure 5:
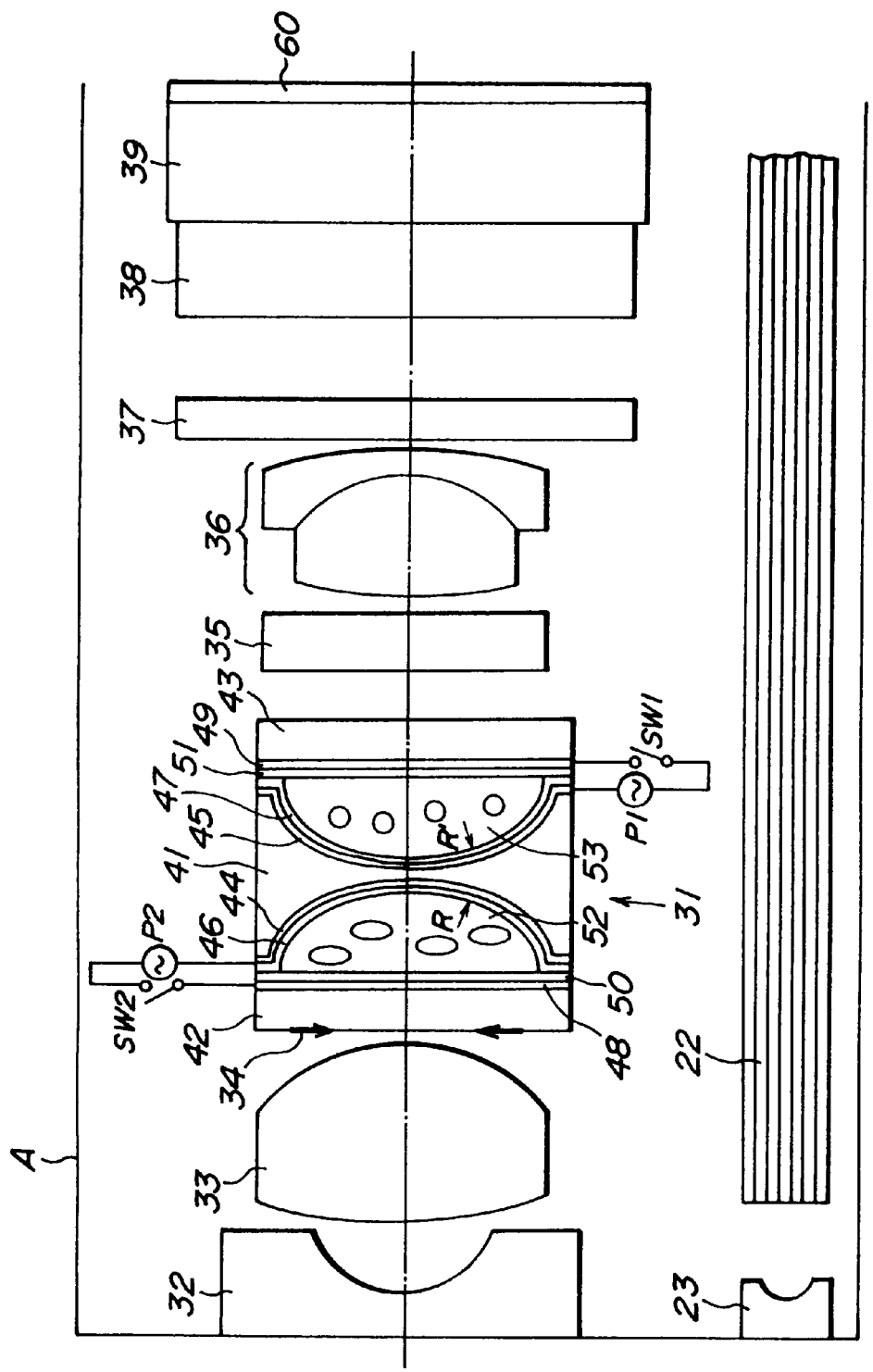
FIG. 5 is an explanatory view showing a construction of third embodiment of an imaging optical system according to the present invention.

FIG. 5 shows a construction of third embodiment of an imaging optical system according to the present invention. This embodiment is a modification of the second embodiment. In this embodiment, the bi-concave lens 41 for forming the liquid crystal lens 41 has its both concave surfaces with slightly different radius curvatures R, R'.

According to this embodiment, the image optical system is formed as the above construction, thereby compensating the above slight run-out of major ray (maximum image height) due to the polarizing direction on the end surface of the CCD.

Figure 6:
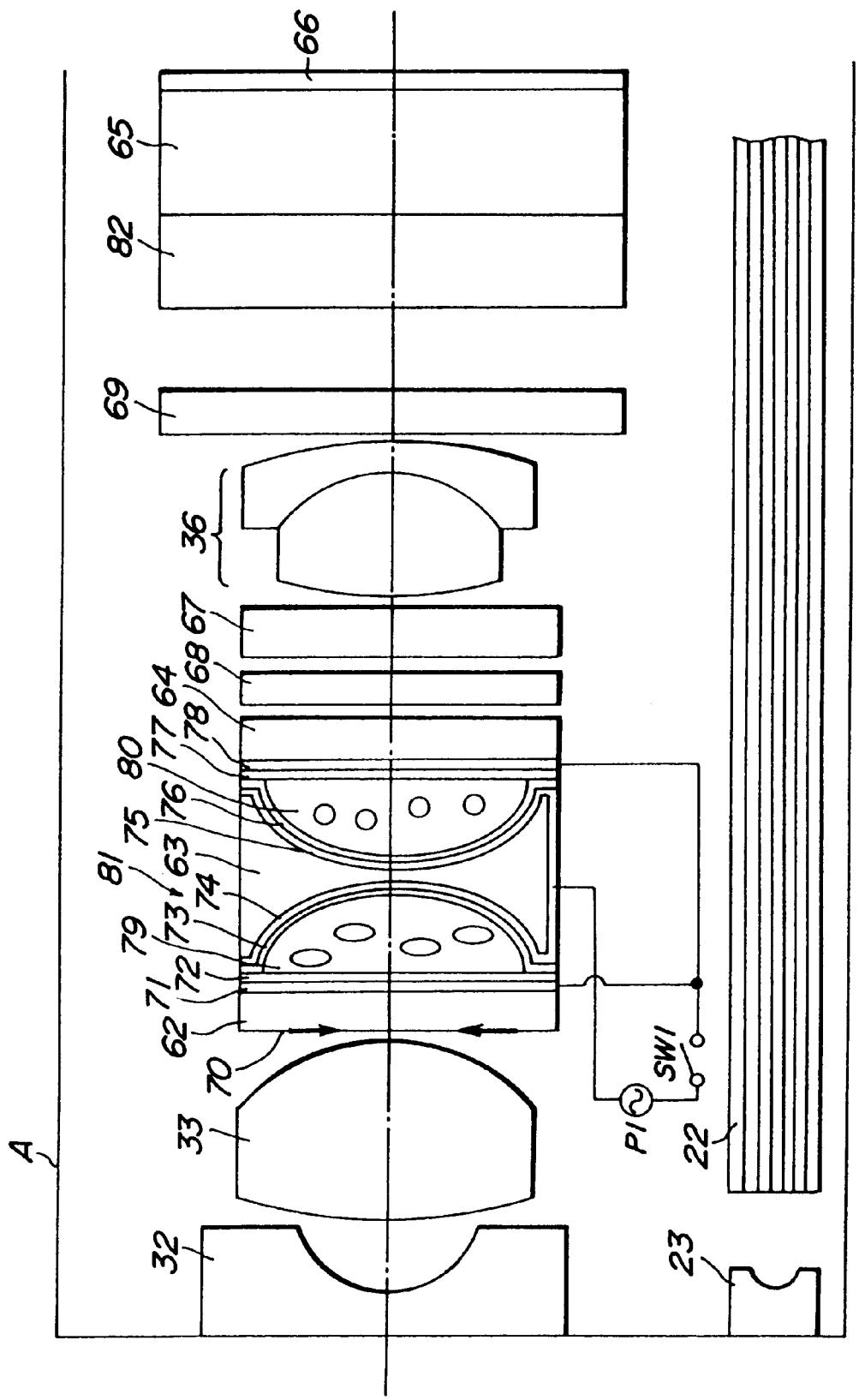
FIG. 6 is an explanatory view showing a construction of fourth embodiment of an imaging optical system according to the present invention.

FIG. 6 shows a construction of fourth embodiment of an imaging optical system according to the present invention, and designates the condition of applying no voltage on the liquid crystal. The imaging optical system of the fourth embodiment is intended to load on an electroscope for digestive organs. This embodiment can intensifies focal depth at near point side by providing a variable focusing function of the liquid crystal lens without substantially changing the lens length and the outer diameter of whole optical system with the use of conventional imaging optical system. Moreover, in the present embodiment, particularly, the light ray height is low near the aperture diaphragm, so that the liquid crystal having lens diameter of 2 mm or the like, thereby making the liquid crystal layer thin and making the response speed of the liquid crystal lens fast, A liquid crystal 81 of this embodiment comprises a plant-parallel plate lenses 62, a bi-concave lens 63 and a plane-parallel plate lenses 64 and the other optical systems of this embodiment are the same construction as in the second embodiment. In this embodiment, also, a solid state imaging element (CCD) 66 is disposed after a cover glass 65 for the solid state imaging element, before which an optical element 82 is disposed, and an image is focused on the end surface of the CCD.

In FIG. 6, also, a plane-parallel plate 67 is an infrared cutting filter for correcting a spectral sensitivity of CCD, and plane-parallel plates 68, 69 are a filter coated by a coat for cutting a TAG laser light utilized for a diagnosis and a remedy. Plane-parallel plate lens or a concave lens which constitute the liquid crystal lens, therefore, is constructed by an infrared cutting filter. Moreover, the YAG laser cutting coat is coated on both surface of the liquid crystal lens, resulting in a compacting. The liquid crystal lens 81 is, also, provided with electrodes on a side surface of the lens, and both surfaces of the bi-concave lens and both of two plane-parallel plates are conductive, simultaneously, thereby driving the liquid crystal lens by only a pair of driving portion.

In the above respective embodiments, the imaging optical system is applied to the endoscope or the like, but the present invention is not limited to such an application, the imaging optical system may be applied to other optical system. Moreover, the above illuminating optical system can also be omitted.

Hereinafter, numerical values of the above first to fourth embodiments are explained, wherein OB is object position up to the best object point position, f is focal length, FNO is F number, IH is image height, $r_1$, $r_2$, ..., is radius of curvature, $d_1$, $d_2$, ..., is distances of respective surfaces, $n_1$, $n_2$, ..., is refractive index at D line (587,56 nm ray) in respective optical members and $v_1$, $v_2$, ..., is abbe's number thereof.

[First Embodiment]

Figure 7:
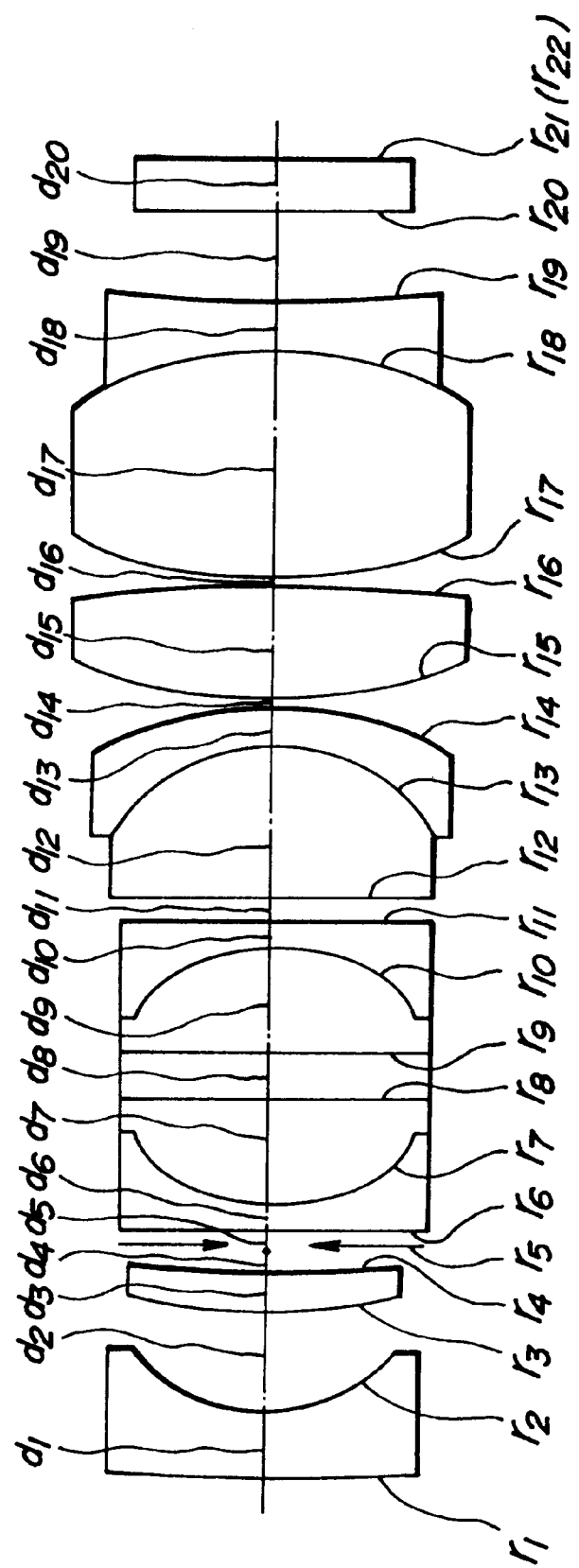
FIG. 7 is an explanatory view defining radius of curvature of respective optical elements and its surface intervals in the first embodiment of the present invention.

(1) Numerical value of optical system (As to definition of respective numerical value, refer to FIG. 7)

| | | | |
|---|---|---|---|
| $r_1$ = 30.655 | $d_1$ = 0.800 | $n_1$ = 1.88 | $v_1$ = 40.78 |
| $r_2$ = 2.206 | $d_2$ = 2.850 | | |
| $r_3$ = 7.352 | $d_3$ = 0.700 | $n_2$ = 1.85 | $v_2$ = 23.78 |
| $r_4$ = 25.586 | $d_4$ = 0.850 | | |
| $r_5$ = ∞ (aperture diaphragm) | $d_5$ = 0.154 | | |
| $r_6$ = ∞ | $d_6$ = 0.480 | $n_3$ = 1.88 | $v_3$ = 40.78 |
| $r_7$ = 27.008 | $d_7$ = 0.020 | $n_a$ (nematic liquid crystal layer) | |
| $r_8$ = ∞ | $d_8$ = 0.300 | $n_4$ = 1.88 | $v_4$ = 40.78 |
| $r_9$ = ∞ | $d_9$ = 0.020 | $n_b$ (nematic liquid crystal layer) | |
| $r_{10}$ = −27.008 | $d_{10}$ = 0.480 | $n_5$ = 1.88 | $v_5$ = 40.78 |
| $r_{11}$ = ∞ | $d_{11}$ = 0.600 | | |
| $r_{12}$ = ∞ | $d_{12}$ = 2.000 | $n_6$ = 1.59 | $v_6$ = 61.18 |
| $r_{13}$ = −2.439 | $d_{13}$ = 0.500 | $n_7$ = 1.85 | $v_7$ = 23.78 |
| $r_{14}$ = −4.515 | $d_{14}$ = 0.100 | | |
| $r_{15}$ = 6.855 | $d_{15}$ = 1.420 | $n_8$ = 1.73 | $v_8$ = 54.68 |
| $r_{16}$ = −32.264 | $d_{16}$ = 0.100 | | |
| $r_{17}$ = 5.532 | $d_{17}$ = 3.070 | $n_9$ = 1.73 | $v_9$ = 54.68 |
| $r_{18}$ = 4.295 | $d_{18}$ = 0.600 | $n_{10}$ = 1.85 | $v_{10}$ = 23.78 |
| $r_{19}$ = 21.640 | $d_{19}$ = 1.390 | | |
| $r_{20}$ = ∞ | $d_{20}$ = 0.700 | $n_{11}$ = 1.52 | $v_{11}$ = 64.15 |
| $r_{21}$ = ∞ | $d_{21}$ = 0 | | |
| $r_{22}$ = (image position) | | | |

In this case, the refraction index of the nematic liquid crystal layer to be used at the ordinary ray is 1.52, the refraction index at the extraordinary ray is 1.76, the aperture diameter of the aperture diaphragm is 1.2 mm.

(2) Numerical value in case of applying the voltage on the nematic liquid crystal layer of the optical system.

| | |
|---|---|
| $n_a$ = 1.52 | $n_b$ = 1.52 |
| OB = 18.3 (mm) | f = 1.4722 (mm) |
| $F_{NO}$ = 2.795 | IH = 1.135 (mm) |

(3) Numerical value in case of performing incidence of the polarized light having oscillating direction parallel to the major axis direction of liquid crystal molecule, under the state of applying voltage on the nematic liquid crystal of the optical system.

| | |
|---|---|
| $n_a$ = 1.76 | $n_b$ = 1.52 |
| OB = 8 (mm) | f = 1.462 (mm) |
| $F_{NO}$ = 2.78 | IH = 1.135 (mm) |

(4) Numerical value in case of performing incidence of the polarized light having oscillating direction perpendicular to the major axis direction of liquid crystal molecule, under the state of applying no voltage on the nematic liquid crystal of the optical system.

| | | | |
|---|---|---|---|
| $n_a$ = 1.52 | $n_b$ = 1.76 | | |
| OB = 8 (mm) | f = 1.464 (mm) | | |
| $F_{NO}$ = 2.79 | IH = 1.135 (mm) | | |

[Second embodiment]

Figure 8:
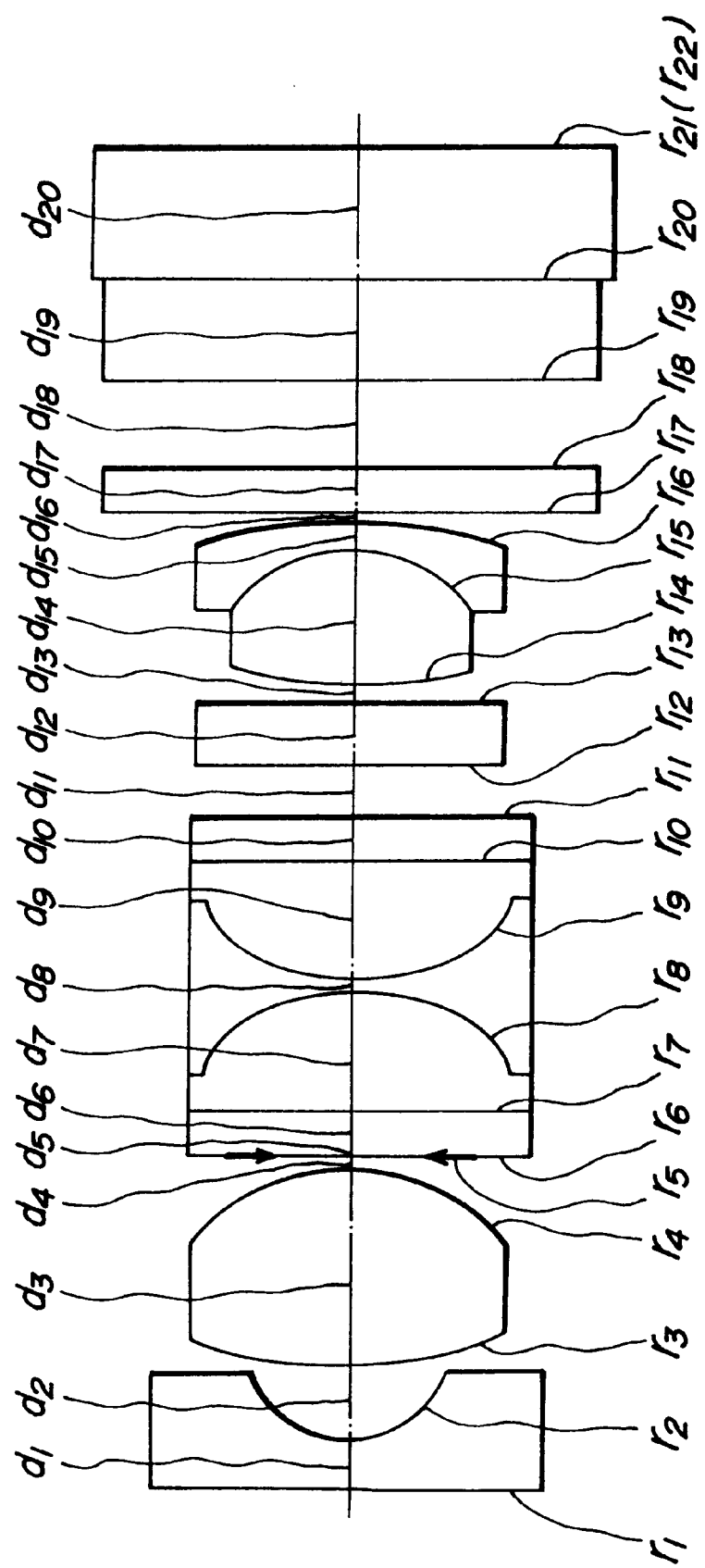
FIG. 8 is an explanatory view defining radius of curvature of respective optical elements and its surface intervals in the second and third embodiments of the present invention.

(1) Numerical value of optical system (As to definition of respective numerical value, refer to FIG. 8)

| | | | |
|---|---|---|---|
| $r_1 = \infty$ | $d_1$ = 0.450 | $n_1$ = 1.88 | $v_1$ = 40.78 |
| $r_2$ = 1.007 | $d_2$ = 0.730 | | |
| $r_3$ = 5.905 | $d_3$ = 2.120 | $n_2$ = 1.77 | $v_2$ = 49.60 |
| $r_4$ = 1.999 | $d_4$ = 0.100 | | |
| $r_5 = \infty$ (aperture diaphragm) | $d_5$ = 0 | | |
| $r_6 = \infty$ | $d_6$ = 0.370 | $n_3$ = 1.52 | $v_3$ = 64.15 |
| $r_7 = \infty$ | $d_7$ = 0.020 | $n_a$ (nematic liquid crystal layer) | |
| $r_8$ = 27.008 | $d_8$ = 0.300 | $n_4$ = 1.52 | $v_3$ = 64.15 |
| $r_9$ = 27.008 | $d_9$ = 0.020 | $n_b$ (nematic liquid crystal layer) | |
| $r_{10} = \infty$ | $d_{10}$ = 0.370 | $n_5$ = 1.52 | $v_5$ = 64.15 |
| $r_{11} = \infty$ | $d_{11}$ = 0.030 | | |
| $r_{12} = \infty$ | $d_{12}$ = 0.620 | $n_6$ = 1.51 | $v_6$ = 75.00 |
| $r_{13} = \infty$ | $d_{13}$ = 0.160 | | |
| $r_{14}$ = 5.781 | $d_{14}$ = 1.300 | $n_7$ = 1.70 | $v_7$ = 55.53 |
| $r_{15}$ = −1.442 | $d_{15}$ = 0.280 | $n_8$ = 1.85 | $v_8$ = 23.78 |
| $r_{16}$ = −5.018 | $d_{16}$ = 0.100 | | |
| $r_{17} = \infty$ | $d_{17}$ = 0.400 | $n_9$ = 1.52 | $v_9$ = 59.89 |
| $r_{18} = \infty$ | $d_{18}$ = 0.871 | | |
| $r_{19} = \infty$ | $d_{19}$ = 1.000 | $n_{10}$ = 1.52 | $v_{10}$ = 64.15 |
| $r_{20} = \infty$ | $d_{20}$ = 1.250 | $n_{11}$ = 1.53 | $v_{11}$ = 59.89 |
| $r_{21} = \infty$ | $d_{21}$ = 0 | | |
| $r_{22}$ (image position) | | | |

In this case, the refraction index of the nematic liquid crystal layer to be used at the ordinary ray is 1.52, the refraction index at the extraordinary ray is 1.76, the aperture diameter of the aperture diaphragm is 1.4 mm.

(2) Numerical value in case of applying the voltage on the nematic liquid crystal layer of the optical system.

| | |
|---|---|
| $n_a$ = 1.52 | $n_b$ = 1.52 |
| OB = 15.0 (mm) | f = 1.609 (mm) |
| $F_{NO}$ = 7.39 | IH = 1.63 (mm) |

(3) Numerical value in case of performing incidence of the polarized light having oscillating direction parallel to the major axis direction of liquid crystal molecule, under the state of applying voltage on the nematic liquid crystal of the optical system.

| | |
|---|---|
| $n_a$ = 1.76 | $n_b$ = 1.52 |
| OB = 8 (mm) | f = 1.570 (mm) |
| $F_{NO}$ = 7.37 | IH = 1.63 (mm) |

(4) Numerical value in case of performing incidence of the polarized light having oscillating direction perpendicular to the major axis direction of liquid crystal molecule, under the state of applying no voltage on the nematic liquid crystal of the optical system.

[Third embodiment]

(1) Numerical value of optical system (As to definition of respective numerical value, refer to FIG. 8)

| | | | |
|---|---|---|---|
| $r_1 = \infty$ | $d_1$ = 0.450 | $n_1$ = 1.88 | $v_1$ = 40.78 |
| $r_2$ = 1.007 | $d_2$ = 0.730 | | |
| $r_3$ = 5.905 | $d_3$ = 2.120 | $n_2$ = 1.77 | $v_2$ = 49.60 |
| $r_4$ = 1.999 | $d_4$ = 0.100 | | |
| $r_5 = \infty$ (aperture diaphragm) | $d_5$ = 0 | | |
| $r_6 = \infty$ | $d_6$ = 0.370 | $n_3$ = 1.52 | $v_3$ = 64.15 |
| $r_7 = \infty$ | $d_7$ = 0.020 | $n_a$ (nematic liquid crystal layer) | |
| $r_8$ = −16.807 | $d_8$ = 0.300 | $n_4$ = 1.52 | $v_4$ = 64.15 |
| $r_9$ = 28.685 | $d_9$ = 0.020 | $n_b$ (nematic liquid crystal layer) | |
| $r_{10} = \infty$ | $d_{10}$ = 0.370 | $n_5$ = 1.52 | $v_5$ = 64.15 |
| $r_{11} = \infty$ | $d_{11}$ = 0.030 | | |
| $r_{12} = \infty$ | $d_{12}$ = 0.620 | $n_6$ = 1.51 | $v_6$ = 75.00 |
| $r_{13} = \infty$ | $d_{13}$ = 0.160 | | |
| $r_{14}$ = 5.781 | $d_{14}$ = 1.300 | $n_7$ = 1.70 | $v_7$ = 55.53 |
| $r_{15}$ = −1.442 | $d_{15}$ = 0.280 | $n_8$ = 1.85 | $v_8$ = 23.78 |
| $r_{16}$ = −5.018 | $d_{16}$ = 0.100 | | |
| $r_{17} = \infty$ | $d_{17}$ = 0.400 | $n_9$ = 1.52 | $v_9$ = 59.89 |
| $r_{18} = \infty$ | $d_{18}$ = 0.871 | | |
| $r_{19} = \infty$ | $d_{19}$ = 1.000 | $n_{10}$ = 1.52 | $v_{10}$ = 64.15 |
| $r_{20} = \infty$ | $d_{20}$ = 1.250 | $n_{11}$ = 1.53 | $v_{11}$ = 59.89 |
| $r_{21} = \infty$ | $d_{21}$ = 0 | | |
| $r_{22}$ (image position) | | | |

In this case, the refraction index of the nematic liquid crystal layer to be used at the ordinary ray is 1.52, the refraction index at the extraordinary ray is 1.76, the aperture diameter of the aperture diaphragm is 0.54 mm (2) Numerical value in case of applying the voltage on the nematic liquid crystal layer of the optical system.

| | |
|---|---|
| $n_a$ = 1.52 | $n_b$ = 1.52 |
| OB = 15.0 (mm) | f = 1.608 (mm) |
| $F_{NO}$ = 7.39 | IH = 1.63 (mm) |

(3) Numerical value in case of performing incidence of the polarized light having oscillating direction parallel to the major axis direction of liquid crystal molecule, under the state of applying no voltage on the nematic liquid crystal of the optical system.

| | |
|---|---|
| $n_a$ = 1.76 | $n_b$ = 1.52 |
| OB = 8 (mm) | f = 1.571 (mm) |
| $F_{NO}$ = 7.37 | IH = 1.63 (mm) |

(4) Numerical value in case of performing incidence of the polarized light having oscillating direction perpendicular to the major axis direction of liquid crystal molecule, under the state of applying no voltage on the nematic liquid crystal of the optical system.

| | |
|---|---|
| $n_a = 1.52$ | $n_b = 1.76$ |
| OB = 8 (mm) | f = 1.547 (mm) |
| $F_{NO} = 7.26$ | IH = 1.63 (mm) |

[Fourth embodiment]

(1) Numerical value of optical system (As to definition of respective numerical value, refer to FIG. 9)

| | | | |
|---|---|---|---|
| $r_1 = \infty$ | $d_1 = 0.460$ | $n_1 = 1.88$ | $v_1 = 40.78$ |
| $r_2 = 1.009$ | $d_2 = 0.830$ | | |
| $r_3 = 5.908$ | $d_3 = 2.120$ | $n_2 = 1.77$ | $v_2 = 49.60$ |
| $r_4 = -2.000$ | $d_4 = 0.100$ | | |
| $r_5 = \infty$ (aperture diaphragm) | $d_5 = 0$ | | |
| $r_6 = \infty$ | $d_6 = 0.300$ | $n_3 = 1.56$ | $v_3 = 60.67$ |
| $r_7 = \infty$ | $d_7 = 0.014$ | $n_a$ (nematic liquid crystal layer) | |
| $r_8 = -16.304$ | $d_8 = 0.250$ | $n_4 = 1.56$ | $v_4 = 60.67$ |
| $r_9 = 16.304$ | $d_9 = 0.014$ | $n_b$ (nematic liquid crystal layer) | |
| $r_{10} = \infty$ | $d_{10} = 0.300$ | $n_5 = 1.56$ | $v_5 = 60.67$ |
| $r_{11} = \infty$ | $d_{11} = 0.030$ | | |
| $r_{12} = \infty$ | $d_{12} = 0.400$ | $n_6 = 1.52$ | $v_6 = 59.89$ |
| $r_{13} = \infty$ | $d_{13} = 0.030$ | | |
| $r_{14} = \infty$ | $d_{14} = 0.620$ | $n_7 = 1.51$ | $v_7 = 75.00$ |
| $r_{15} = \infty$ | $d_{15} = 0.079$ | | |
| $r_{16} = 5.772$ | $d_{16} = 1.300$ | $n_8 = 1.70$ | $v_8 = 55.53$ |
| $r_{17} = -1.273$ | $d_{17} = 0.280$ | $n_{10} = 1.85$ | $v_{10} = 23.78$ |
| $r_{18} = -5.020$ | $d_{18} = 0.100$ | | |
| $r_{19} = \infty$ | $d_{19} = 0.400$ | $n_{11} = 1.52$ | $v_{11} = 59.89$ |
| $r_{20} = \infty$ | $d_{20} = 0.890$ | | |
| $r_{21} = \infty$ | $d_{22} = 1.000$ | $n_{12} = 1.52$ | $v_{12} = 64.15$ |
| $r_{22} = \infty$ | $d_{22} = 1.250$ | $n_{13} = 1.52$ | $v_{13} = 59.89$ |
| $r_{23} = \infty$ | $d_{23} = 0$ | | |
| $r_{24}$ (image position) | | | |

In this case, the refraction index of the nematic liquid crystal layer to be used at the ordinary ray is 1.52, the refraction index at the extraordinary ray is 1.76, the aperture diameter of the aperture diaphragm is 0.37 mm.

(2) Numerical value in case of applying the voltage on the nematic liquid crystal layer of the optical system.

| | |
|---|---|
| $n_a = 1.52$ | $n_b = 1.52$ |
| OB = 10.0 (mm) | f = 1.597 (mm) |
| $F_{NO} = 11.14$ | IH = 1.63 (mm) |

(3) Numerical value in case of performing incidence of the polarized light having oscillating direction parallel to the major axis direction of liquid crystal molecule, under the state of applying no voltage on the nematic liquid crystal of the optical system.

| | |
|---|---|
| $n_a = 1.76$ | $n_b = 1.52$ |
| OB = 3.7 (mm) | f = 1.597 (mm) |
| $F_{NO} = 11.14$ | IH = 1.63 (mm) |

(4) Numerical value in case of performing incidence of the polarized light having oscillating direction perpendicular to the major axis direction of liquid crystal molecule, under the state of applying no voltage on the nematic liquid crystal of the optical system.

| | |
|---|---|
| $n_a = 1.52$ | $n_b = 1.76$ |
| OB = 3.7 (mm) | f = 1.597 (mm) |
| $F_{NO} = 11.28$ | IH = 1.63 (mm) |

FIG. 10 shows whole construction of the distal section for an endoscope described in respective embodiments. The endoscope 130 comprises an endoscope unit 120 having a distal section A accommodating therein an optical system for imaging and an optical system for illumination and a member for transmitting a picked-up image and the illuminating light, a monitor 125 and a light source 127. A subject imaged at the distal section A is displayed finally at the monitor 125 as an image for the endoscope and observed by an observer. The illuminating light from the light source 127 illuminates a field of view direction through a light guide cable 126, base section 123, an inserting section 122 and the distal section A (light guide 22 and the illuminating lens 23).

What is claimed is:

1. An imaging optical system comprising an optical member including a first body consisting of a substantially transparent birefringent liquid crystal member, a second body consisting of a substantially transparent birefringent liquid crystal member, and at least a pair of electrodes for adding an electric field or a magnetic field onto the first body and the second body, a rear face of the first body being aligned perpendicular to a front face of the second body, and the difference of birefringence Δn of the liquid crystal and the absolute value |R| of radius of curvature of the first body and the second body satisfy the following relation:

$$0.005 \leq \Delta n / |R| \leq 0.1.$$

2. An imaging optical system as claimed in claim 1, wherein the first body and the second body are formed so that a plate, a biconcave lens and a plane lens are laminated; and liquid crystals are disposed in air gaps formed between the plate, biconcave lens and plane lens.

3. An imaging optical system comprising an optical member including a first body consisting of a substantially transparent birefringent liquid crystal member, a second body consisting of a substantially transparent birefringent liquid crystal member, and at least a pair of electrodes for adding an electric field or a magnetic field onto the first body and the second body, a rear face of the first body being aligned perpendicular to a front face of the second body, and a distance L between the optical member and an aperture diaphragm and a focal length f of whole imaging optical system satisfy following relation:

$$L \leq f/2.$$

4. An imaging optical system as claimed in claim 3, wherein the optical member is placed just before or just after an aperture diaphragm.

5. An imaging optical system as claimed in claim 3, wherein the first body and the second body have a substantially symmetrical shape against a plane perpendicular to an optical axis, the substantially symmetrical shape of the first body and the second body is a convex surface, and these convex surfaces are displaced opposite to each other.

6. An imaging optical system as claimed in claim 3, wherein the absolute value |R| of radius curvature of the first body and the second body satisfies following relation:

$$1 \text{ (mm)} \leq |R| \leq 80 \text{ (mm)}.$$

7. An imaging optical system as claimed in claim 3, wherein a distance $L_{12}$ between the first body and the second body satisfies following relation:

$$0.1 \text{ (mm)} \leq L_{12} \leq 0.4 \text{ (mm)}.$$

8. An imaging optical system as claimed in claim 3, wherein assuming that the thickness of the first body and the second body is d, an absolute value of radium curvature of the first body and the second body is |R|, and an aperture diaphragm radius of the first body and the second body is D, the following relation is satisfied:

$$D^2/8|R| \leq d \leq 0.04 \text{ (mm)}.$$

9. An imaging optical system as claimed in claim 3, wherein the difference of birefringence Δn of the liquid crystal of the first body and the second body satisfies following relation:

$$0.15 \leq \Delta n \leq 0.35.$$

10. An imaging optical system comprising an optical member including a first body and a second body each consisting of a substantially transparent birefringent liquid crystal member, and at least a pair of electrodes for adding an electric field or a magnetic field onto the first body and the second body, a front face of the first body being aligned perpendicular to a rear face of the second body, a rear face of the first body is made of a concave surface facing the front face of the first body, and a front face of the second body is made of a concave surface facing a rear face of the second body, and said concave surfaces are displaced opposite to each other.

11. An imaging optical system as claimed in claim 10, wherein a distance $L_{12}$ between the first body and the second body satisfies following relation:

$$0.1 \text{ (mm)} \leq L_{12} \leq 0.4 \text{ (mm)}.$$

12. An imaging optical system as claimed in claim 10, wherein the absolute value |R| of radius curvature of the first body and the second body satisfies following relation:

$$1 \text{ (mm)} \leq |R| \leq 80 \text{ (mm)}.$$

13. An imaging optical system comprising an optical member including a first body consisting of a substantially transparent birefringent liquid crystal member, a second body consisting of a substantially transparent birefringent liquid crystal member, and at least a pair of electrodes for adding an electric field or a magnetic field onto the first body and the second body, a rear face of the first body being aligned perpendicular to a front face of the second body, and a distance $L_{12}$ between the first body and the second body satisfies following relation:

$$0.1 \text{ (mm)} \leq L_{12} \leq 0.4 \text{ (mm)}.$$

14. An imaging optical system as claimed in claim 13, wherein the first body and the second body have an asymmetric shape to a surface perpendicular to an optical axis.

15. An imaging optical system as claimed in claim 14, wherein the absolute values $|R_1|, |R_2|$ of radius curvature of the first body and the second body satisfy following relation:

$$0.5 \leq |R_1/R_2| \leq 2.$$

16. An imaging optical system as claimed in claim 13, wherein the absolute value |R| of radius curvature of the first body and the second body satisfies following relation:

$$1 \text{ (mm)} \leq |R| \leq 80 \text{ (mm)}.$$

17. An imaging optical system as claimed in claim 13, wherein assuming that the thickness of the first body and the second body is d, an absolute value of radius curvature of the first body and the second body is |R|, and an aperture diaphragm radius of the first body and the second body is D, the following relation is satisfied:

$$D^2/8|R| \leq d \leq 0.04 \text{ (mm)}.$$

18. An imaging optical lens as claimed in claim 13, wherein an outer diameter of the optical member is less than φ5 mm.

19. An imaging optical system as claimed in claim 18, wherein the substrate filling the first body and the second body therein is constructed by an infrared ray cutting filter.

* * * * *